United States Patent
Bianchi et al.

(10) Patent No.: US 8,731,663 B2
(45) Date of Patent: May 20, 2014

(54) VAGAL STIMULATION DURING ATRIAL TACHYARRHYTHMIA TO FACILITATE CARDIAC RESYNCHRONIZATION THERAPY

(71) Applicants: Stefano Bianchi, Rome (IT); Pietro Rossi, Rome (IT)

(72) Inventors: Stefano Bianchi, Rome (IT); Pietro Rossi, Rome (IT)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/749,438

(22) Filed: Jan. 24, 2013

(65) Prior Publication Data

US 2013/0138173 A1 May 30, 2013

Related U.S. Application Data

(63) Continuation of application No. 12/496,528, filed on Jul. 1, 2009, now Pat. No. 8,386,038.

(51) Int. Cl.
*A61N 1/00* (2006.01)

(52) U.S. Cl.
USPC .......................................................... 607/14

(58) Field of Classification Search
USPC ...................................... 607/14, 3, 8, 44, 122
See application file for complete search history.

(56) References Cited

U.S. PATENT DOCUMENTS

| | | | |
|---|---|---|---|
| 4,951,667 A | 8/1990 | Markowitz et al. | |
| 5,154,170 A | 10/1992 | Bennett et al. | |
| 5,203,326 A | 4/1993 | Collins | |
| 5,243,980 A | 9/1993 | Mehra | |
| 5,320,642 A | 6/1994 | Scherlag | |
| 5,330,507 A | 7/1994 | Schwartz | |

(Continued)

FOREIGN PATENT DOCUMENTS

| | | |
|---|---|---|
| EP | 0547734 A2 | 6/1993 |
| EP | 0756507 B1 | 2/1999 |

(Continued)

OTHER PUBLICATIONS

Henning et al., "Vagal nerve stimulation increases right ventricular contraction and relaxation and heart rate," Cardiovascular Research 32: 846-853, 1996.

(Continued)

*Primary Examiner* — Robert N Wieland
(74) *Attorney, Agent, or Firm* — Shumaker & Sieffert, P.A.

(57) ABSTRACT

The disclosure describes techniques for delivering vagal stimulation to decrease the ventricular rate response during an atrial tachyarrhythmia, such as atrial fibrillation. Decreasing the ventricular rate response during an atrial tachyarrhythmia may facilitate increased ventricular pacing for cardiac resynchronization therapy (CRT), and may also reduce the likelihood of inappropriately detecting a ventricular tachyarrhythmia during the atrial tachyarrhythmia. Furthermore, the vagal stimulation may augment vagal tone, which may facilitate long term left ventricular reverse remodeling and decrease atrial and ventricular arrhythmic burden in heart failure patients. An example system that delivers CRT comprises a processor that detects an atrial tachyarrhythmia in one or more atria of the heart, and monitors at least one of a ventricular rate or degree of ventricular pacing subsequent to the detected atrial arrhythmia. The processor controls a stimulation generator to deliver vagal stimulation based on the least one of a ventricular rate or degree of ventricular pacing.

30 Claims, 10 Drawing Sheets

(56) References Cited

U.S. PATENT DOCUMENTS

| | | | |
|---|---|---|---|
| 5,356,425 | A | 10/1994 | Bardy et al. |
| 5,403,356 | A | 4/1995 | Hill et al. |
| 5,411,531 | A | 5/1995 | Hill et al. |
| 5,507,784 | A | 4/1996 | Hill et al. |
| 5,620,468 | A | 4/1997 | Mongeon et al. |
| 5,683,429 | A | 11/1997 | Mehra |
| 5,855,592 | A | 1/1999 | McGee et al. |
| 5,876,422 | A | 3/1999 | van Groeningen |
| 5,978,700 | A | 11/1999 | Nigam |
| 6,256,537 | B1 | 7/2001 | Stoop et al. |
| 6,393,316 | B1 | 5/2002 | Gillberg et al. |
| 6,438,421 | B1 | 8/2002 | Stahmann et al. |
| 6,611,713 | B2 | 8/2003 | Schauerte |
| 6,731,978 | B2 | 5/2004 | Olson et al. |
| 7,138,607 | B2 | 11/2006 | Wang et al. |
| 7,139,607 | B1 | 11/2006 | Shelchuk |
| 7,225,019 | B2 | 5/2007 | Jahns et al. |
| 7,245,967 | B1 | 7/2007 | Shelchuk |
| 8,126,561 | B2 * | 2/2012 | Chavan et al. .................. 607/44 |
| 2002/0035335 | A1 | 3/2002 | Schauerte |
| 2004/0172075 | A1 | 9/2004 | Shafer et al. |
| 2005/0096705 | A1 | 5/2005 | Pastore et al. |
| 2005/0119704 | A1 | 6/2005 | Peters et al. |
| 2005/0261741 | A1 | 11/2005 | Libbus et al. |
| 2006/0206153 | A1 | 9/2006 | Libbus et al. |
| 2006/0206159 | A1 | 9/2006 | Moffitt et al. |
| 2006/0224202 | A1 | 10/2006 | Moffitt et al. |
| 2007/0083242 | A1 | 4/2007 | Mazgalev et al. |
| 2007/0276443 | A1 * | 11/2007 | Shafer et al. ...................... 607/3 |
| 2008/0091240 | A1 | 4/2008 | Ben-David et al. |
| 2008/0269819 | A1 | 10/2008 | Zhou |
| 2009/0005845 | A1 * | 1/2009 | David et al. .................... 607/122 |
| 2010/0036447 | A1 | 2/2010 | Zhang et al. |
| 2011/0004262 | A1 | 1/2011 | Bianchi et al. |
| 2011/0015690 | A1 * | 1/2011 | Ryu et al. ........................ 607/14 |

FOREIGN PATENT DOCUMENTS

| | | |
|---|---|---|
| EP | 1426078 A1 | 6/2004 |
| EP | 1870129 A1 | 12/2007 |
| WO | 0189526 A1 | 11/2001 |
| WO | 2007142563 A1 | 12/2007 |
| WO | 2008144125 A1 | 11/2008 |

OTHER PUBLICATIONS

Rossi et al., "Post-operative atrial fibrillation management by selective epicardial vagal fat pad stimulation," J Interv Card Electrophysiol (2009) 24:37-45.

Bianchi et al., "Endocardial Transcatheter Stimulation of the AV Nodal Fat Pad: Stabilization of Rapid Ventricular Rate Response During Atrial Fibrillation in Left Ventricular Failure," Journal of Cardiovascular Electrophysiology 20 (1):103-105, Jan. 2009.

Schwartz et al., "Long term vagal stimulation in patients with advanced heart failure: first experience in man," Eur J. Heart Fail, Sep. 2008;10(9): 884-91.

Poole et al., "Prognostic importance of defibrillator shocks in patients with heart failure" N Engl J. Med. 2008; 359 (10):1009-17.

Nunain et al., "Limitations and late complications of third-generation automatic cardioverter-defirillators," Circulation 1995;91(8):2204-2213.

Nanthakumar et al., "Inappropriate therapy from atrial fibrillation and sinus tachycardia in automated implantable cardioverter defibrullators," Am Heart J., 2000; 139(5):797-803.

Kale et al., "Atrial septal pacing in the prevention of paroxysmal atrial fibrillation refractory to antiarrhythmic drugs," International Journal of Cardiology 82(2):167-175, Feb. 2002.

Gupta, "Suppression of Paroxysmal Atrial Fibrillation by Pacing," Indian Pacing and Electrophysiology Journal (ISSN 0972-6292), 3(2):45-46, 2003.

The National Heart, Lung, and Blood Institute for working group on Atrial fibrillation: Current understanding research imperatives, J Am Coll Cardiol 1993; 22(7):1830-34.

Ogawa et al., "Acute Effects of Different Atrial Pacing Sites in Patients with Atrial Fibrillation: Comparison of Single Site and Biatrial Pacing," PACE 2001; 24:1470-78.

Murgatroyd, "Pills and Pulses: Hybrid Therapy for Atrial Fibrillation", J Cardiovasc Electrophysiol vol. 13, pp. S40-S46, Jan. 2002, Suppl.

Carlsson et al., "Therapy of Atrial Fibrillation: Rhythm Control Versus Rate Control," PACE 2000: 23: 891-903.

Harvey et al., "Radiofrequency catheter ablation for atrial fibrillation," Coronary Artery Disease 1995; 6(2):115-20.

Rosenqvist et al., "Relative Importance of Activation Sequence Compared to Atrioventricular Synchrony in Left Ventricular Function," Am J Cardiol 1991; 67:148-156.

Vardas et al., "AAIR versus DDDR Pacing in Patients with Impaired Sinus Node Chronotropy: An Echocardiographic and Cardiopulmonary Study," PACE 1997: 20;1762-64.

Israel et al, "Atrial Pacing in the Prevention of Paroxysmal Atrial Fibrillation: First Results of a New Combined Algorithm," PACE 2000; 23[Pt.II]: 1888-1890.

Saksena et al., "Prevention of Atrial fibrillation by pacing." In Barold SS and Mugica J (Eds), 1998. Recent Advances in Cardiac Pacing: Goals for the 21st century. Armonk, NY. Futura Publishing Company Inc., pp. 101-114.

Levine et al.,"Pacing for the Suppression of Paroxysmal Atrial Fibrillation in an 87-year-old Patient," Indian Pacing Electrophysiol. J. 2003; 3: 88.

Purerfellner et al., "Accuracy of Atrial Tachyarrhythmia Detection in Implantable Devices with Arrhythmia Therapies," PACE 2004; 27(7):983-992.

Tosato et al., "Closed-loop control of the heart rate by electrical stimulation of the vagus nerve," Med Biol Eng Comp 44(3):161-169, 2006.

Zhang et al., "Optimal ventricular rate slowing during atrial fibrillation by feedback AV nodal-selective vagal stimulation," Am J Physiol Heart Circ Physiol 2002; 282(3):H1102-H1110.

Zhang et al., "Chronic Atrioventricular Nodal Vagal Stimulation: First Evidence for Long-Term Ventricular Rate Control in Canine Atrial Fibrillation Model," Circulation 2005; 112:2904-2911.

Zhuang et al., "Ventricular Rate Control by Selective Vagal Stimulation is Superior to Rhythm Regularization by Atrioventricular Nodal Ablation and Pacing During Atrial Fibrillation," Circulation 2002; 106(14):1853-1858.

International Search Report and Written Opinion from corresponding PCT Application Serial No. PCT/EP2010/003956 dated Nov. 4, 2010 (11 pages).

U.S. Appl. No. 12/845,505, by Arun Kumar et al., filed Jul. 28, 2010.

Wilkoff et al., Critical Analysis of Dual-Chamber Implantable Cardioverter-Defibrillator Arthythmial Detection: Results and Technical Considerations, Circulation, (Jan. 23, 2001), pp. 381-386, vol. 103, No. 3.

International Search Report, PCT/US/2008/059723, Aug. 27, 2008, 6 pages.

Written Opinion, PCT/US/2008/059723, Aug. 27, 2008, 7 pages.

International Preliminary Report on Patentability, PCT/US/2008/059723, Oct. 27, 2009, 8 pages.

Office Action for U.S. Appl. No. 11/740,565, mailed Dec. 30, 2009, 8 pages.

Responsive Amendment to Office Action for U.S. Appl. No. 11/740,565, filed Apr. 29, 2010, 10 pages.

Final Office Action for U.S. Appl. No. 11/740,565, mailed Jan. 21, 2011, 9 pages.

Responsive Amendment to Office Action for U.S. Appl. No. 11/740,565, filed Mar. 21, 2011, 8 pages.

Aydin M. Bilgutay et al., "Vagal tuning and new concept in treatment of supraventricular arrhythmias, angina pectoris, and heart failure," Journal of Thoracic and Cardiovascular Surgery, vol. 56, No. 1 (Jul. 1968) pp. 71-82.

Reply to Written Opinion from corresponding application serial No. PCT/EP2010/003956 (WO2011/000558) dated May 2, 2011 (4 pages).

International Preliminary Report on Patentability of international application No. PCT/EP2010/003956, dated Jul. 20, 2011, 10 pp.

(56) References Cited

OTHER PUBLICATIONS

Bilgutay, A.M. et al., "Vagal tuning: A new concept in the treatment of supraventricular arrhythmias, angina pectoris, and heart failure," The Journal of Thoracic and Cardiovascular Surgery (0022-5223) Jul. 1968 vol. 56, Iss. 1, pp. 71-82.

European Examination Report from corresponding European Application No. 10729699.8 dated Oct. 18, 2012 (4 pages).
Office Action from Japanese application No. 2012-518049, dated Jun. 18, 2013, 3 pp.
Office Action from Japanese application No. 2012-518049, dated Oct. 24, 2013, 2 pp.

* cited by examiner

VAGAL STIMULATION DURING ATRIAL TACHYARRHYTHMIA TO FACILITATE CARDIAC RESYNCHRONIZATION THERAPY

This application is a continuation of U.S. patent application Ser. No. 12/496,528, filed Jul. 1, 2009 and issued as U.S. Pat. No. 8,386,038 on Feb. 26, 2013, the entire content of which is incorporated herein by reference.

TECHNICAL FIELD

The invention relates to medical devices and, more particularly, to medical devices that deliver electrical stimulation therapy.

BACKGROUND

When functioning properly, a heart maintains its own intrinsic rhythm, and is capable of pumping adequate blood throughout a circulatory system. This intrinsic rhythm is a function of intrinsic signals generated by the sinoatrial node, or SA node, located in the upper right atrium. The SA node periodically depolarizes, which in turn causes the atrial heart tissue to depolarize such that right and left atria contract as the depolarization travels through the atrial heart tissue. The atrial depolarization signal is also received by the atrioventricular node, or AV node, which, in turn, triggers a subsequent ventricular depolarization signal that travels through and depolarizes the ventricular heart tissue causing the right and left ventricles to contract.

Some patients, however, have irregular cardiac rhythms, referred to as cardiac arrhythmias. Cardiac arrhythmias result in diminished blood circulation because of diminished cardiac output. Atrial fibrillation is a common cardiac arrhythmia that reduces the pumping efficiency of the heart. Atrial fibrillation is characterized by rapid, irregular, uncoordinated depolarizations of the atria. These depolarizations may not originate from the SA node, but may instead originate from an arrhythmogenic substrate, such as an ectopic focus, within the atrial heart tissue. The reduced pumping efficiency due to atrial fibrillation requires the ventricle to work harder, which is particularly undesirable in sick patients that cannot tolerate additional stresses. As a result of atrial fibrillation, patients must typically limit activity and exercise.

An even more serious problem, however, is the induction of rapid and irregular ventricular heart rhythms by the atrial fibrillation. Irregular atrial depolarization signals associated with atrial fibrillation are received by the AV node and may be conducted to ventricles. During atrial fibrillation, the intervals between ventricular depolarizations may be shortened and vary substantially. Such induced ventricular arrhythmias compromise pumping efficiency even more drastically than atrial arrhythmias. This phenomenon is referred to as rapidly conducted atrial fibrillation, or "conducted AF."

Patients with heart failure are, in some cases, treated with cardiac resynchronization therapy (CRT). CRT is a form of cardiac pacing. In some examples, CRT involves delivery of pacing pulses to both ventricles ("biventricular pacing") to synchronize their contraction. In other examples, CRT involves delivery of pacing pulses to one ventricle to synchronize its contraction with that of the other ventricular, such as pacing the left ventricle to synchronize its contraction with that of the right ventricle. In symptomatic, drug-refractory heart failure patients with prolonged QRS and low ejection fraction, CRT may also provide an effective therapy to produce a reverse remodeling.

SUMMARY

CRT may be more effective as the percentage of ventricular contractions that are paced, and thereby synchronized, is increased. The increased and variable ventricular rate during a conducted atrial tachyarrhythmia may result in more intrinsic ventricular depolarizations and, therefore, less effective CRT. Furthermore, the increased and variable ventricular rate during a conducted atrial tachyarrhythmia may be misinterpreted by a medical device with cardioversion and/or defibrillation capabilities as a ventricular tachyarrhythmia, which may lead to delivery of an unneeded therapy to the patient.

In general the disclosure is directed toward delivering vagal stimulation to decrease the ventricular rate response to a conducted atrial tachyarrhythmia. Stimulation of the epicardial fat pad that projects parasympathetic nerve fibers from the vagus nerve to the AV node, which is referred to herein as AV nodal vagal stimulation and is one example of vagal stimulation, induces a decrease in mean ventricular rate during atrial fibrillation without significant inotropic impairment and with an improvement in hemodynamics. The AV node nerve fibers can be selectively stimulated endocardially at the postero- and anteroseptal right atrium and at the proximal coronary sinus.

Vagal stimulation, such as AV-nodal vagal stimulation, may reduce the ventricular rate response to an atrial tachyarrhythmia. In this manner, the vagal stimulation may allow a greater percentage of ventricular contractions to be paced. Because CRT is more effective as the percentage of ventricular contractions that are paced is increased, vagal stimulation during atrial tachyarrhythmia may be particularly beneficial for patients receiving CRT. Vagal stimulation during atrial tachyarrhythmia may also reduce the likelihood of inappropriately detecting a ventricular tachyarrhythmia during the atrial tachyarrhythmia. Furthermore, the vagal stimulation may augment vagal tone, which may facilitate long term left ventricular reverse remodeling and decrease atrial and ventricular arrhythmic burden in heart failure patients.

In one example, a method comprises delivering cardiac resynchronization therapy to at least one ventricle of a heart of a patient, detecting an atrial tachyarrhythmia of the heart during the delivery of the cardiac resynchronization therapy, detecting an extent of ventricular rate response to the detected atrial tachyarrhythmia, and delivering vagal stimulation during the delivery of the cardiac resynchronization therapy and the detected atrial tachyarrhythmia based on the extent of the ventricular rate response.

In another example, a system comprises a stimulation generator and a processor. The stimulation generator is configured to deliver cardiac resynchronization therapy to at least one ventricle of a heart of a patient and vagal stimulation to the patient. The processor is configured to detect an atrial tachyarrhythmia of the heart during the delivery of the cardiac resynchronization therapy, detect an extent of ventricular rate response to the detected atrial tachyarrhythmia, and control the stimulation generator to deliver the vagal stimulation during the delivery of the cardiac resynchronization therapy and the detected atrial tachyarrhythmia based on the extent of the ventricular rate response.

In another example, a computer-readable medium comprises instructions for causing a programmable processor to control delivery of cardiac resynchronization therapy to at least one ventricle of a heart of a patient, detect an atrial tachyarrhythmia of the heart during the delivery of the cardiac resynchronization therapy, detect at an extent of ventricular rate response to the detected atrial tachyarrhythmia, and control delivery of vagal stimulation during the delivery of the cardiac resynchronization therapy and the detected atrial tachyarrhythmia based on the extent of the ventricular rate response.

In another example, a system comprises means for delivering cardiac resynchronization therapy to at least one ventricle of a heart of a patient, means for detecting an atrial tachyarrhythmia of the heart during the delivery of the cardiac resynchronization therapy, means for detecting an extent of ventricular rate response to the detected atrial tachyarrhythmia, and means for delivering vagal stimulation during the delivery of the cardiac resynchronization therapy and the detected atrial tachyarrhythmia based on the ventricular rate response.

The details of one or more examples are set forth in the accompanying drawings and the description below. Other features, objects, and advantages will be apparent from the description and drawings, and from the claims.

DETAILED DESCRIPTION

In general, the disclosure is directed toward delivering vagal stimulation. Vagal stimulation may help regulate the cardiac autonomic nervous system by increasing parasympathetic activity, which may reduce the ventricular rate response to a conducted atrial tachyarrhythmia. An atrial tachyarrhythmia may be an atrial fibrillation or atrial tachycardia, as examples.

Due to the close relation of vagal innervation to the atrioventricular (AV) node, high frequency stimulation, e.g., in the form of bursts of pulses or a continuous train of pulses, of the AV node and/or neural fibers proximate to the AV node may provide such vagal stimulation. Additionally, AV nodal vagal stimulation may block atrial signals from propagating to the ventricles, which may also reduce the ventricular rate response to a conducted atrial tachyarrhythmia. Hereinafter, vagal stimulation will be primarily described with respect to the example of AV nodal stimulation. However, in other examples, vagal stimulation may be delivered at other locations, such epicardially at one or more fat pads, or directly to the vagus nerve via, for example, a cuff electrode.

AV nodal or other vagal stimulation may be particularly useful in patients receiving cardiac resynchronization therapy (CRT), e.g., biventricular pacing of both the right and left ventricles, to resynchronize a heart whose ventricles do not contract in synchrony. CRT may be more effective as the percentage of ventricular contractions that are paced rather than intrinsic increases. An atrial tachyarrhythmia may induce rapid and irregular ventricular depolarizations, and thereby cause the percentage of intrinsic ventricular contractions to increase.

A medical device, e.g., the same medical device that delivers the CRT, may detect an atrial tachyarrhythmia, and monitor the intrinsic ventricular rate or the percentage of paced and/or intrinsic ventricular contractions subsequent to the detected atrial arrhythmia. If the ventricular rate is above a threshold or the extent of pacing is below a threshold, e.g., the percentage of paced ventricular contractions is below a threshold value and/or the percentage of intrinsic ventricular contractions is above a threshold value, the medical device may deliver AV nodal or other vagal stimulation to reduce the ventricular rate response to the atrial tachyarrhythmia. The AV nodal vagal stimulation may decrease the amount of ventricular depolarizations propagated from the atria and increase the percentage of ventricular depolarizations that are paced.

Figure 1:
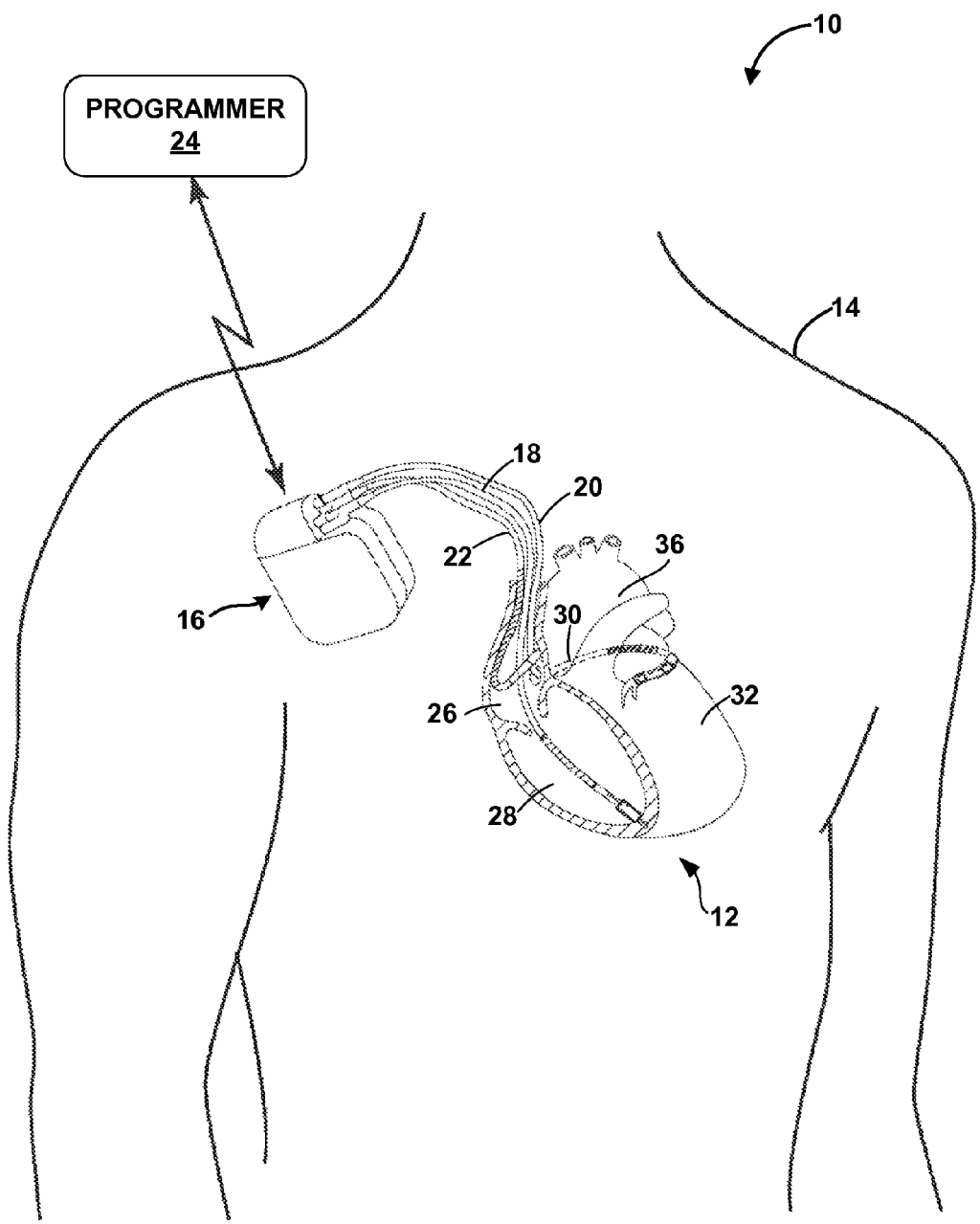
FIG. 1 is a conceptual diagram illustrating an example therapy system comprising an implantable medical device (IMD) that may be used to monitor one or more physiological parameters of a patient and/or provide therapy to the heart of a patient.

FIG. 1 is a conceptual diagram illustrating an example therapy system 10 that may be used to monitor one or more physiological parameters of patient 14 and/or to provide therapy to heart 12 of patient 14. Therapy system 10 includes an implantable medical device (IMD) 16, which is coupled to leads 18, 20, and 22, and programmer 24. IMD 16 may be an implantable pacemaker that provides electrical signals to heart 12 via electrodes coupled to one or more of leads 18, 20, and 22. In addition to pacing therapy, IMD 16 may deliver AV nodal stimulation and/or neurostimulation signals. In some examples, IMD 16 may also include cardioversion and/or defibrillation functionalities. Patient 12 is ordinarily, but not necessarily, a human patient.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. RV lead 18 may be used to deliver RV pacing to heart 12. Left ventricular (LV) lead 20 extends through one or more veins, the vena cava, right atrium 26, and into the coronary sinus 30 to a region adjacent to the free wall of left ventricle 32 of heart 12. LV lead 20 may be used to deliver LV pacing to heart 12.

In some examples, LV lead 20 may be used in combination with RV lead 18 to deliver biventricular pacing to heart 12, which may provide cardiac resynchronization therapy (CRT) to heart 12. CRT may be used to treat heart failure-inducted conduction disturbances and/or ventricular dyssynchrony. In some cases, CRT may help restore the mechanical sequence of ventricular activation and contraction. In some examples, CRT may involve biventricular pacing, e.g., via RV lead 18 and LV lead 20, to synchronize the contraction of both ventricles. In other examples, CRT may involve pacing one of the ventricles, e.g., LV 32 via LV lead 20, to synchronize its contraction with that of the other ventricle.

Right atrial (RA) lead 22 extends through one or more veins and the vena cava, and into the right atrium 26 of heart 12. RA lead 22 may be positioned in the inferior portion of right atrium 26. In some examples, RA lead 22 may be positioned in the posterior portion of right atrium 26 around the coronary sinus ostium, such as posteriorly to the coronary sinus ostium, and along the septum that separates right atrium 26 and left atrium 36. For example, RA lead 22 may be positioned such that RA lead 22 may sense electrical activity within right atrium 26, pace right atrium 26, and also deliver a stimulation signal to or proximate to the AV node, e.g., to or proximate to the AV nodal vagal fat pad.

In some alternative examples, therapy system 10 may include an additional lead or lead segment (not shown in FIG. 1) that deploys one or more electrodes within the vena cava or other vein, or within or near the aorta. In other alternative examples, system 10 may include one or more additional intravenous or extravascular leads or lead segments that deploy one or more electrodes epicardially, e.g., near an epicardial fat pad, or proximate to the vagal nerve. In other alternative examples, system 10 need not include one of ventricular leads 18 and 20, such as where CRT is provided by pacing one ventricle, rather than both ventricles.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar.

IMD 16 may trigger ventricular pacing, e.g., RV, LV, or biventricular pacing, based on atrial depolarizations sensed via RA lead 22. As another example, RA lead 22 may deliver atrial pacing, and IMD 16 may trigger ventricular pacing based on atrial-paced events. In some examples, RV lead 18 and/or LV lead 20 may sense ventricular depolarizations, and IMD 16 may trigger ventricular pacing, e.g., RV, LV, or biventricular pacing, based on whether RV lead 18 and/or LV lead 20 detects an intrinsic ventricular depolarization within a defined time interval following the atrial sensed or paced event. The time interval between an atrial sensed or paced event and delivery of a pacing pulse to one or more of the ventricles may be referred to as an AV interval.

IMD 16 may also provide neurostimulation therapy, defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art. IMD 16 may similarly deliver antitachycardia pacing or cardioversion in response to detecting tachycardia of ventricles 28 and 32. IMD 16 may also detect an atrial tachyarrhythmia, such as atrial fibrillation, and deliver AV nodal vagal stimulation to reduce the ventricular rate response to the atrial tachyarrhythmia.

In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, or other clinician, interacts with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14 or information derived from sensed physiological parameters, such as an indication of the extent of ventricular pacing, as described herein. As another example, the user may use programmer 24 to retrieve information from IMD 16 regarding the performance or integrity of IMD 16 or other components of system 10, such as leads 18, 20 and 22, or a power source of IMD 16. As another example, the user may interact with programmer 24 to program, e.g., select parameters for, therapies provided by IMD 16, such as pacing and AV nodal stimulation and, optionally, cardioversion and/or defibrillation.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
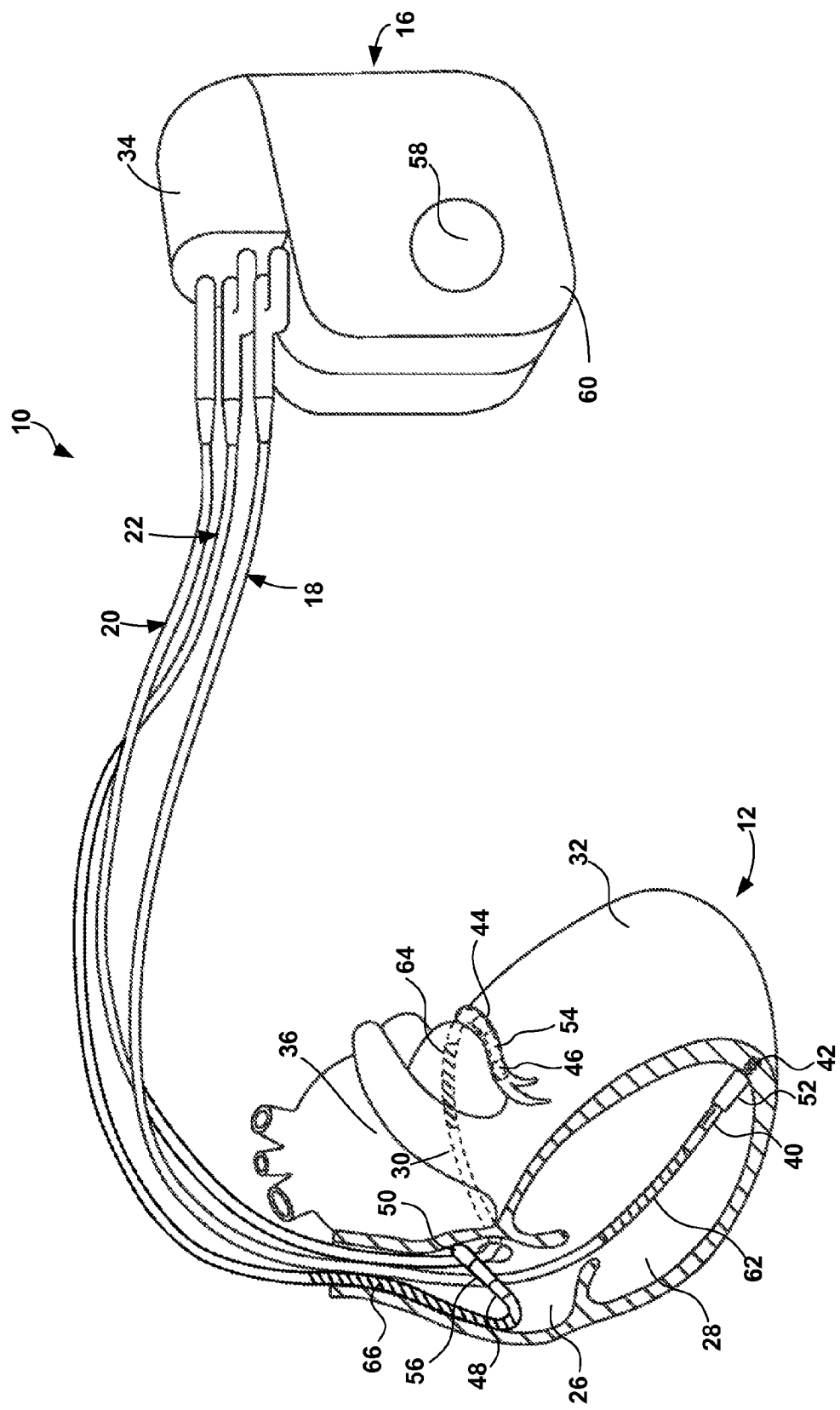
FIG. 2 is a conceptual diagram further illustrating the IMD and leads of the system of FIG. 1 in conjunction with the heart.

FIG. 2 is a conceptual diagram illustrating IMD 16 and leads 18, 20, 22 of therapy system 10 in greater detail. Leads 18, 20, 22 may be electrically coupled to a signal generator and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in left ventricle 32 and bipolar electrodes 48 and 50 are located adjacent to a distal end of lead 22 in right atrium 26.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In some examples, one or more of electrodes 42, 46, and 50 may take the form of pre-exposed helix tip electrodes. In other examples, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

Helix tip electrode 50, which may be extendable or pre-exposed, of RA lead 22 may be inserted into the tissue of right atrium 26 to substantially fix RA lead 22 within right atrium 26. For example, helix tip electrode 50 may be inserted into or proximate to the endocardium of the septum that separates right atrium 26 and left atrium 36 at a posterior portion of right atrium 26. As described previously, RA lead 22 may be positioned such that RA lead 22 may sense electrical activity within right atrium 26, and also deliver a stimulation signal to (or proximate to) the AV node, e.g., to (or proximate to) the AV nodal vagal fat pad. Helix tip electrode 50 may aid in maintaining RA lead 50 in the appropriate position to provide such functionality.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 3, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor coupled to housing electrode 58. IMD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. For example, electrodes 40, 42, and/or 58 may be used to deliver RV pacing to heart 12. Additionally or alternatively, electrodes 44, 46, and/or 58 may be used to deliver LV pacing to heart 12, and electrodes 48, 50 and/or 58 may be used to deliver RA pacing to heart 12. As described previously, RV pacing, e.g., via electrodes 40, 42, and/or 58, may be used in combination with LV pacing, e.g., via electrodes 44, 46, and/or 58, to synchronize contraction of both ventricles. This type of biventricular pacing may be referred to as cardiac resynchronization therapy (CRT).

IMD 16 may deliver AV nodal vagal stimulation via electrodes 48, 50, and/or 66 of RA lead 22, e.g., in a bipolar configuration or in a unipolar configuration in combination with housing electrode 58. For example, IMD 16 may detect an atrial tachyarrhythmia, e.g., via any combination of electrodes 48, 50, 56 and 58, and deliver AV nodal vagal stimulation in response to the detection. The AV nodal vagal stimulation may reduce the ventricular rate response to the atrial tachyarrhythmia.

Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

Figure 3:
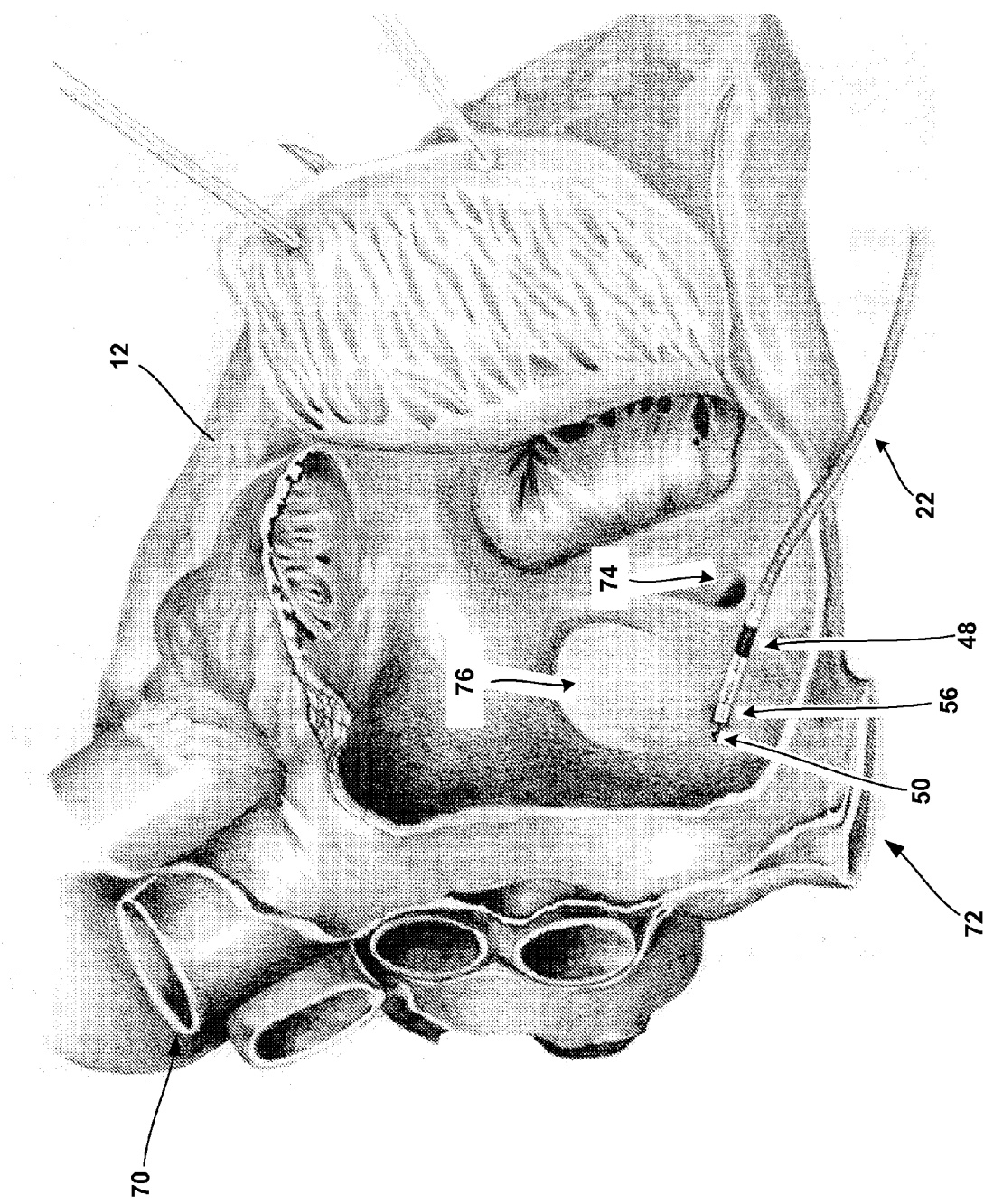
FIG. 3 is a conceptual diagram illustrating an example implantation location for a right atrial lead through which AV nodal vagal stimulation may be delivered.

FIG. 3 is a conceptual diagram illustrating an example implantation location for RA lead 22, through which AV nodal vagal stimulation may be delivered. FIG. 3 illustrates heart 12 with right atrium 26 exposed by dissection and retraction of outer wall of the right atrium. Although not illustrated in FIG. 3, the distal portion of RA lead 22 will generally be advanced to its implantation location within right atrium 26 intravenously and through superior vena cava 70 (or, in some cases, inferior vena cava 72). In the illustrated example, the distal portion of RA lead 22 is positioned and implanted in the posterior portion of right atrium 26, posteriorly to the coronary sinus ostium 74 and along the septum 76 that separates right atrium 26 and left atrium 36. Helical tip electrode 50 may engage the endocardial tissue to fix the distal portion lead 22 at this position.

Figure 4:
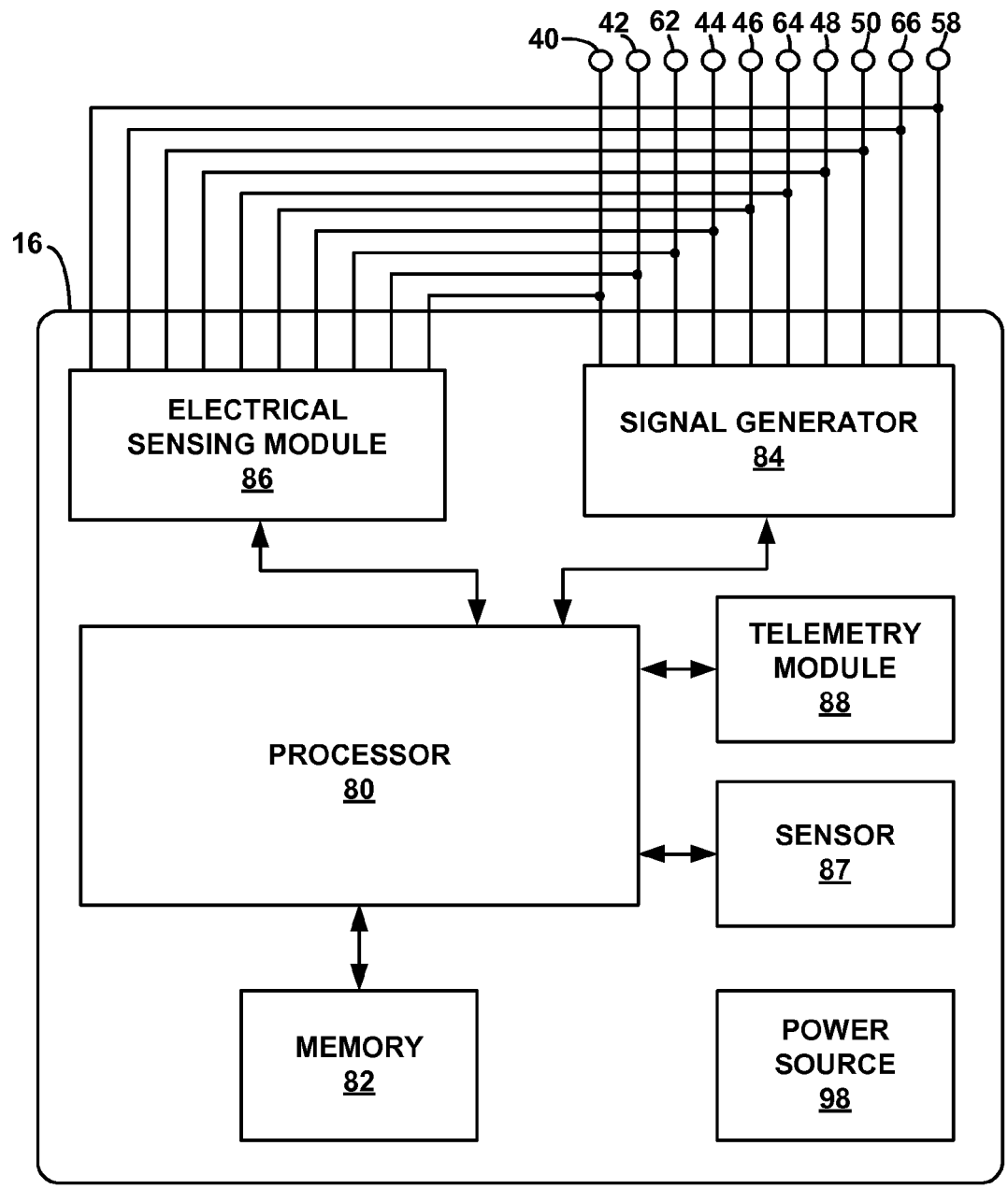
FIG. 4 is a functional block diagram illustrating an example configuration of an IMD.

FIG. 4 is a functional block diagram illustrating one example configuration of IMD 16. In the example illustrated by FIG. 3, IMD 16 includes a processor 80, memory 82, signal generator 84, electrical sensing module 86, sensor 87, telemetry module 88, and power source 98. Memory 82 may include computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls signal generator 84 to deliver stimulation therapy to heart 12 according to operational parameters or programs, which may be stored in memory 82.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. Signal generator 84 may also deliver AV nodal vagal stimulation via electrodes 48, 50, and/or 66 of RA lead 22, e.g., in a bipolar configuration or in a unipolar configuration in combination with housing electrode 58. In some examples, signal generator 84 delivers one or more of these types of stimulation in the form of electrical pulses. In other examples, signal generator 84 may deliver one or more of these types of stimulation in the form of other signals, such as sine waves, square waves, or other substantially continuous time signals.

In some examples, signal generator 84 is configured to deliver AV nodal vagal stimulation in the form of a series of high frequency pulses. For example, signal generator 84 may deliver AV nodal vagal stimulation, e.g., via electrodes 48, 50, and/or 66 of RA lead 22, in a burst pattern characterized by a plurality of pulse trains of high frequency pulses. This burst pattern may be particularly effective in interrupting the conduction of cardiac impulses across the AV node, and modulating the autonomic nervous system via the vagal nerve.

Memory 82 may store values for stimulation parameters that processor 80 accesses to control delivery of AV nodal vagal stimulation by signal generator 84. Such stimulation parameters may include pulse duration, pulse train duration, pulse amplitude, pulse frequency, and pulse train frequency. As one example, signal generator 82 may control stimulation using a pulse duration of approximately 0.2 milliseconds, a pulse train duration of approximately 250 milliseconds, an amplitude of approximately 4 volts, a pulse frequency of approximately 50 hertz, and a pulse train frequency of approximately 80 pulse trains per minute. These values merely are examples and other values are also contemplated.

In some examples, memory 82 may provide a set of values of stimulation parameters for initial delivery of AV nodal vagal stimulation. The values of stimulation parameters may be adjusted based on feedback received during therapy delivery. For example, electrical sensing module 86 may sense the rate of ventricular contraction while signal generator 84 delivers AV nodal vagal stimulation, and processor 80 may control signal generator to modify one or more stimulation parameters based on the ventricular rate.

In some examples, memory 82 may also store suitable ranges for one or more stimulation parameters. As one example, may store a pulse train frequency range of approximately 40 pulse trains per minute to approximately 140 pulse trains per minute. In other examples, the pulse train frequency may fall outside of this range.

Signal generator 84 may include a switch module and processor 80 may use the switch module to select, e.g., via a data/address bus, which of the available electrodes are used to deliver stimulation signals, e.g., defibrillation, pacing, and/or AV nodal vagal stimulation signals. The switch module may include a switch array, switch matrix, multiplexer, or any other type of switching device suitable to selectively couple a signal to selected electrodes.

Electrical sensing module 86 monitors signals from at least one of electrodes 40, 42, 44, 46, 48, 50, 58, 62, 64 or 66 in order to monitor electrical activity of heart 12. Electrical sensing module 86 may also include a switch module to select which of the available electrodes are used to sense the heart activity. In some examples, processor 80 may select the electrodes that function as sense electrodes, or the sensing configuration, via the switch module within electrical sensing module 86, e.g., by providing signals via a data/address bus.

In some examples, electrical sensing module 86 includes multiple detection channels, each of which may comprise an amplifier. Each sensing channel may detect electrical activity in respective chamber of heart 12, and may be configured to detect either R-waves or P-waves. In some examples, electrical sensing module 86 or processor 80 may include an analog-to-digital converter for digitizing the signal received from a sensing channel for electrogram signal processing by processor 80. In response to the signals from processor 80, the switch module within electrical sensing module 86 may couple the outputs from the selected electrodes to one of the detection channels or the analog-to-digital converter.

During pacing, escape interval counters maintained by processor 80 may be reset upon sensing of R-waves and P-waves with respective detection channels of electrical sensing module 86. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one or more of the chambers of heart 12. Processor 80 may control signal generator to deliver a pacing pulse to a chamber upon expiration of an escape interval. Processor 80 may reset the escape interval counters upon the generation of pacing pulses by stimulation generator 84, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals. Processor 80 may use the count in the interval counters to detect a tachyarrhythmia event, such as an atrial or ventricular fibrillation or tachycardia and/or detect a heart rate, such as an atrial rate or ventricular rate.

Processor 80 may also derive other physiological parameters from signals sensed via electrical sensing module 86. For example, processor 80 may establish one or more indicators of ejection fraction and/or heart failure status from electrical signals sensed via electrical sensing module 86. In particular, impedance signals may be used to determine flow or pressure, which may indicate ejection fraction and/or heart failure status.

IMD 16 may also include one or more sensors 87 separate from electrodes 40, 42, 44, 46, 48, 50, 58, 62, 64 and 66. Via a signal generated by sensor 87, processor may monitor one or more physiological parameters indicative of cardiac contraction, autonomic tone, heart failure, and/or ejection fraction. Examples of sensors 87 that may generate a signal indicative of cardiac contraction include a intracardiac or intravascular pressure sensor, an accelerometer or other sensor capable of detecting heart or blood sounds, vibrations, or motion, an optical or ultrasonic sensor capable or detecting changes in flow associated with cardiac contractions, or an optical sensor capable of detecting oxygen saturation changes associated with cardiac contractions. Processor 80 may detect cardiac contractions based on signals from one or more sensors 87, and detect arrhythmias based on the detected cardiac contractions.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and receive downlinked data from programmer 24 via an address/data bus. In some examples, telemetry module 88 may provide received data to processor 80 via a multiplexer.

In some examples, processor 80 transmits indications of detected atrial tachyarrhythmias and the ventricular rate or extent of ventricular pacing subsequent to the detected arrhythmias via telemetry module 88. Processor 80 may also transmit, via telemetry module 88, information regarding AV nodal vagal stimulation delivered by signal generator 84 and a response to AV nodal vagal stimulation, e.g., detected by electrical sensing module 86.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis. In other examples, power source 90 may include a supercapacitor.

Figure 5:
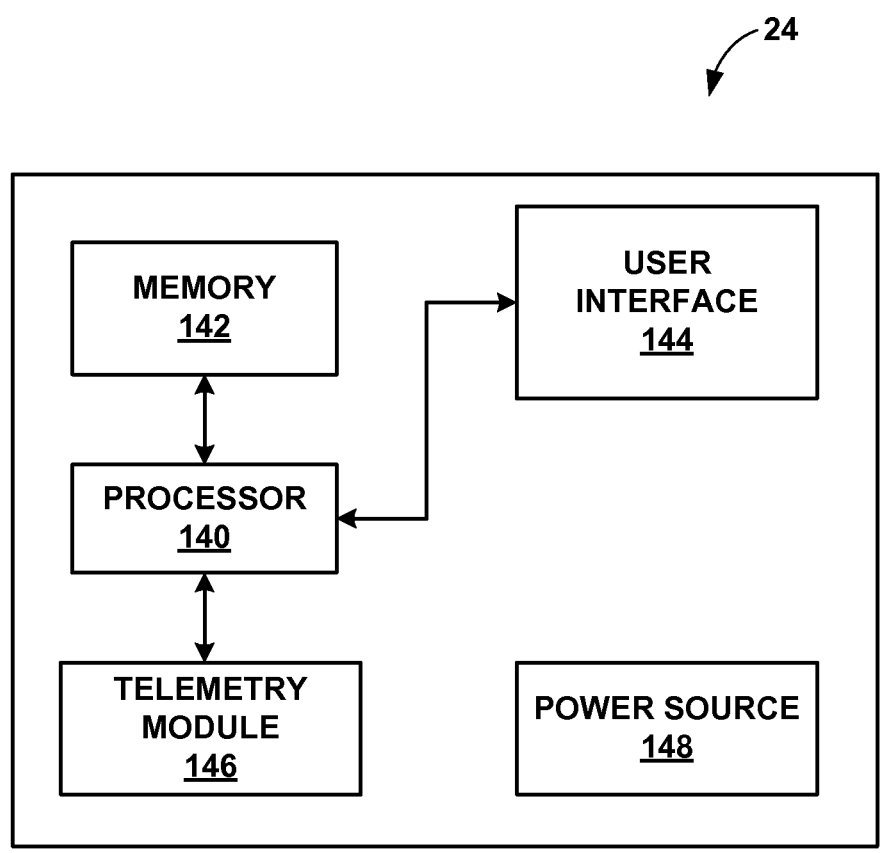
FIG. 5 is block diagram of an example external programmer that facilitates user communication with the IMD.

FIG. 5 is block diagram of an example configuration of programmer 24. As shown in FIG. 5, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of operational parameters), generate new therapy programs, or modify therapy programs for IMD 16. The clinician may interact with programmer 24 via user interface 144 which may include a display to present a graphical user interface to a user, and a keypad or another mechanism for receiving input from a user.

Processor 14 can take the form one or more microprocessors, DSPs, ASICs, FPGAs, programmable logic circuitry, or the like, and the functions attributed to processor 102 herein may be embodied as hardware, firmware, software or any combination thereof. Memory 142 may store instructions that cause processor 140 to provide the functionality ascribed to programmer 24 herein, and information used by processor 140 to provide the functionality ascribed to programmer 24 herein. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 12, as described above with reference to FIG. 1. Telemetry module 146 may be similar to telemetry module 88 of IMD 16 (FIG. 3).

Telemetry module 146 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 140 may be configured to provide some or all of the functionality ascribed to processor 80 of IMD 16 herein. For example, processor 140 may receive indications of cardiac depolarizations or contractions, a signal from one or more sensors 87, or information regarding detected atrial arrhythmias and the ventricular rate or extent of ventricular pacing subsequent to the detected arrhythmias from IMD 16 via telemetry module 146. In some examples, processor 140 may initiate or modify AV nodal vagal stimulation, as described herein with respect to IMD 16 and processor 80.

Figure 6:
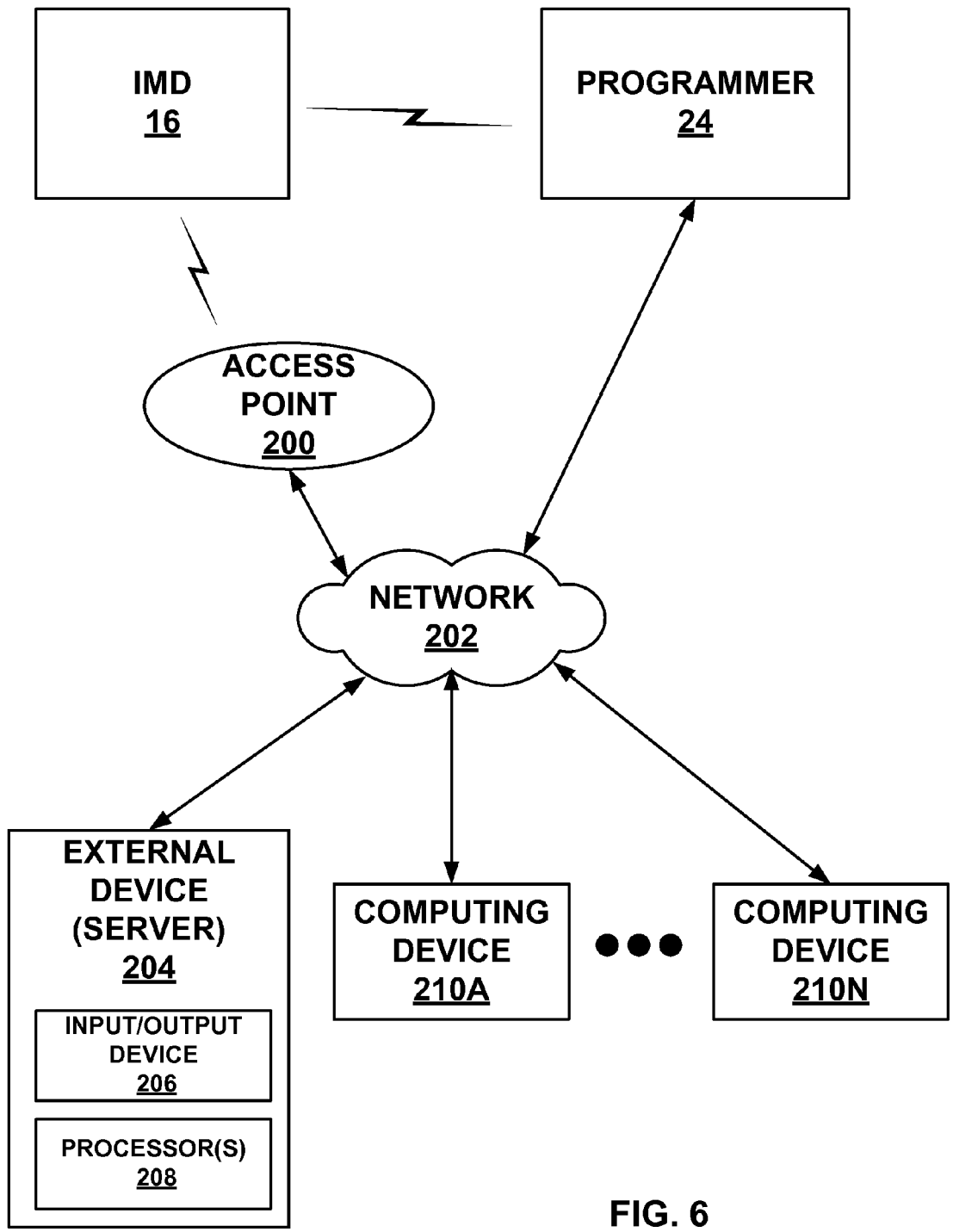
FIG. 6 is a block diagram illustrating an example system that includes an external device, such as a server, and one or more computing devices that are coupled to the IMD and programmer shown in FIG. 1 via a network.

FIG. 6 is a block diagram illustrating an example system that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 5, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 202 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16.

In some cases, server 204 may be configured to provide a secure storage site for data that has been collected from IMD 16 and/or programmer 24. Network 202 may comprise a local area network, wide area network, or global network, such as the Internet. In some cases, programmer 24 or server 206 may assemble data in web pages or other documents for viewing by trained professionals, such as clinicians, via viewing terminals associated with computing devices 210A-210N. The illustrated system of FIG. 6 may be implemented, in some aspects, with general network technology and functionality similar to that provided by the Medtronic CareLink® Network developed by Medtronic, Inc., of Minneapolis, Minn.

In some examples, processor 208 of server 204 may be configured to provide some or all of the functionality ascribed to processor 80 of IMD 16 herein. For example, processor 206 may receive indications of cardiac depolarizations or contractions, a signal from one or more sensors 87, or information regarding detected atrial tachyarrhythmias and the ventricular rate or extent of ventricular pacing subsequent to the detected arrhythmias from IMD 16 via access point 200 or programmer 24 and network 202. Processor 206 may also adjust AV nodal vagal stimulation based on the ventricular rate or extent of ventricular pacing subsequent to the detected tachyarrhythmia. In some examples, server 204 relays received indications of cardiac depolarizations or contractions, a signal from one or more sensors 87, or information regarding detected atrial arrhythmias and the ventricular rate or extent of ventricular pacing subsequent to the detected arrhythmias provided by one or more of IMD 16 or programmer 24 to one or more of computing devices 210 via network 202. A processor of a computing device 210 may provide some or all of the functionality ascribed to processor 80 of IMD 16 herein.

Figure 7:
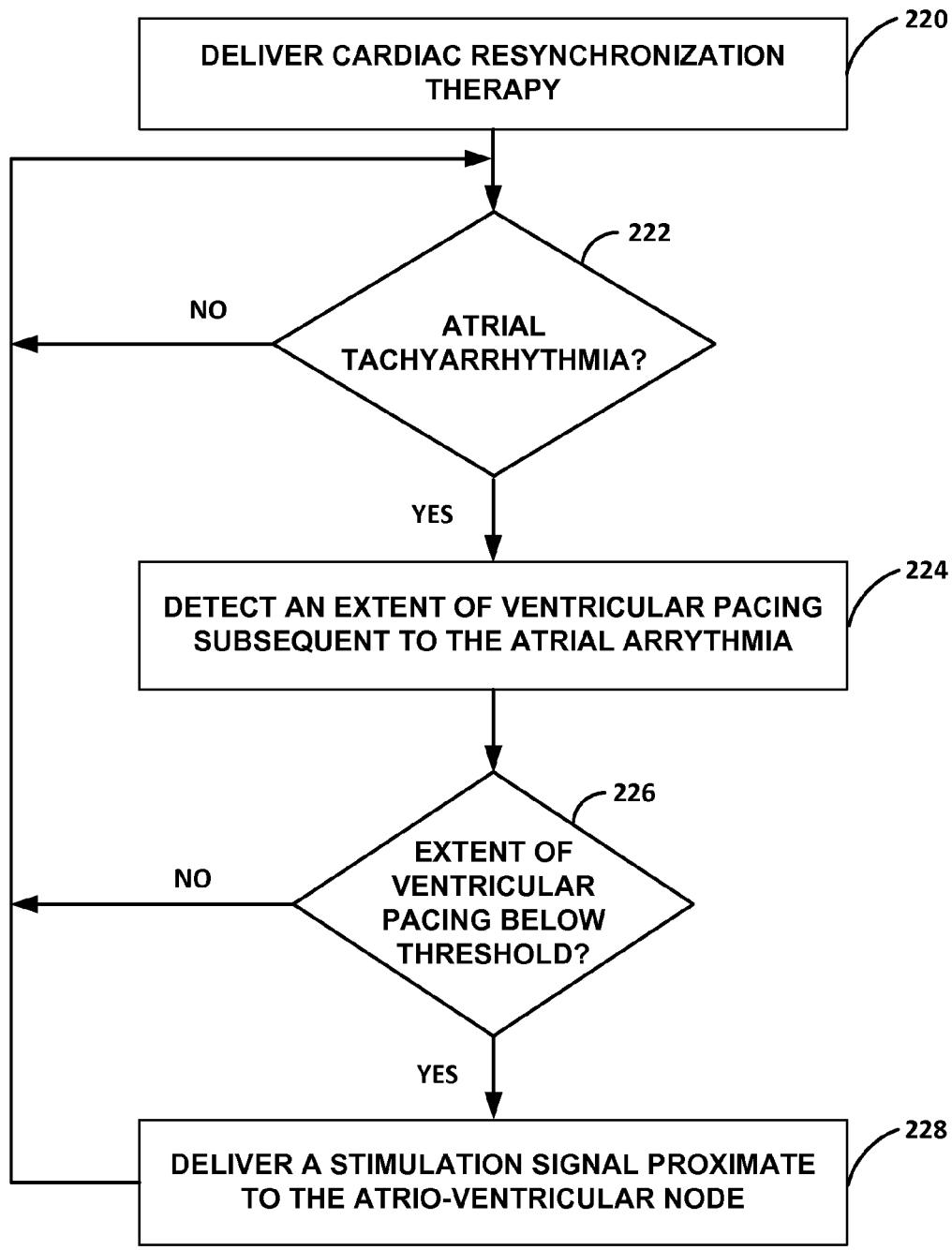
FIG. 7 is a flow diagram of an example method of delivering vagal stimulation to a patient.

FIG. 7 is a flow diagram of an example method of delivering AV nodal vagal stimulation to patient 14. IMD 16 may deliver CRT therapy to patient 14, e.g., by delivering biventricular pacing to RV 28 and LV 32 via RV lead 18 and LV lead 20 (220). CRT may aid in synchronizing contraction of RV 28 and LV 32.

Processor 80 may also monitor atrial depolarizations to determine whether an atrial tachyarrhythmia, such as an atrial fibrillation, is detected (222). For example, processor 80 may monitor atrial depolarization indications received from electrical sensing module 86 to detect the atrial tachyarrhythmia. In response to detecting an atrial tachyarrhythmia, processor 80 may detect an extent of ventricular pacing subsequent to the detected atrial tachyarrhythmia (224). For example, processor 80 may detect at least one of the percentage of ventricular contractions that are paced and the percentage of ventricular contractions that are intrinsic.

The effectiveness of CRT in synchronizing the contraction of RV 28 and LV 32 may decrease as the extent of ventricular pacing decreases. In addition to synchronizing the contraction of RV 28 and LV 32, CRT may also produce reverse remodeling effects, such as long-term improvements of left ventricular function and functional capacity. In patients that experience atrial tachyarrhythmia, these effects may be diminished as the percentage of ventricular contractions that are paced decreases and the percentage of ventricular contractions that are intrinsic increases due to the ventricular rate response to the atrial tachyarrhythmia.

To evaluate the impact of the detected atrial tachyarrhythmia, e.g., the extent of the ventricular rate response to the atrial tachyarrhythmia, processor 80 may, in some examples, compare the extent to which ventricular contractions are paced to a threshold (226). For example, processor 80 may determine whether the percentage of ventricular contractions that are paced is below a threshold. As another example, processor 80 may determine whether the percentage of ventricular contractions that are intrinsic exceeds a threshold. In other examples, instead of or in addition to detecting the extent of ventricular pacing, processor 80 evaluates the extent of the ventricular rate response based on the ventricular rate. For example, processor 80 may monitor the ventricular rate subsequent to the detected atrial tachyarrhythmia, e.g., based on indications of ventricular depolarizations received from electrical sensing module 86.

In the illustrated example, if the extent of ventricular pacing is below the threshold, processor 80 controls signal generator 84 to deliver a stimulation signal proximate to the AV node of heart 12 of patient 14 (228). The AV nodal stimulation may be configured to modulate the autonomic nervous system via the vagus nerve and/or at least particularly block atrial contractions from propagating to RV 28 and/or LV 32 to control the ventricular rate response. When the ventricular rate response is adequately controlled, the CRT pacing delivered by signal generator 84 may control the timing of ventricular contractions. For example, in the absence of sensed ventricular depolarizations, signal generator 84 may deliver pacing pulses for CRT upon expiration of an AV, A-RV, or A-LV interval timer.

In some examples, substantially all intrinsic ventricular contractions are inhibited when signal generator 84 delivers AV nodal vagal stimulation. In such examples, substantially all of the ventricular contractions that occur while signal generator 84 delivers AV nodal vagal stimulation are paced. In this manner, IMD 16 may control the ventricular rate and provide CRT during an atrial tachyarrhythmia.

In some examples, IMD 16 may deliver cardioversion and/or defibrillation therapy to right ventricle 28 and/or left ventricle 32 in response to detecting a fast ventricular rate, e.g., via electrical sensing module 86. Slowing the ventricular rate using AV nodal vagal stimulation during an atrial tachyarrhythmia, such as atrial fibrillation, may prevent IMD 16 from initiating a cardioversion and/or defibrillation shock during the atrial tachyarrhythmia. In this manner, the AV nodal vagal stimulation delivered by signal generator 84 may increase the effectiveness of CRT and/or prevent signal generator 84 from initiating cardioversion and/or defibrillation therapy in response to an atrial tachyarrhythmia. Additionally, the vagal tone augmentation provided by AV nodal vagal stimulation may improve long-term left ventricular reverse remodeling and decrease atrial and ventricular arrhythmic burden in heart failure patients.

Figure 8:
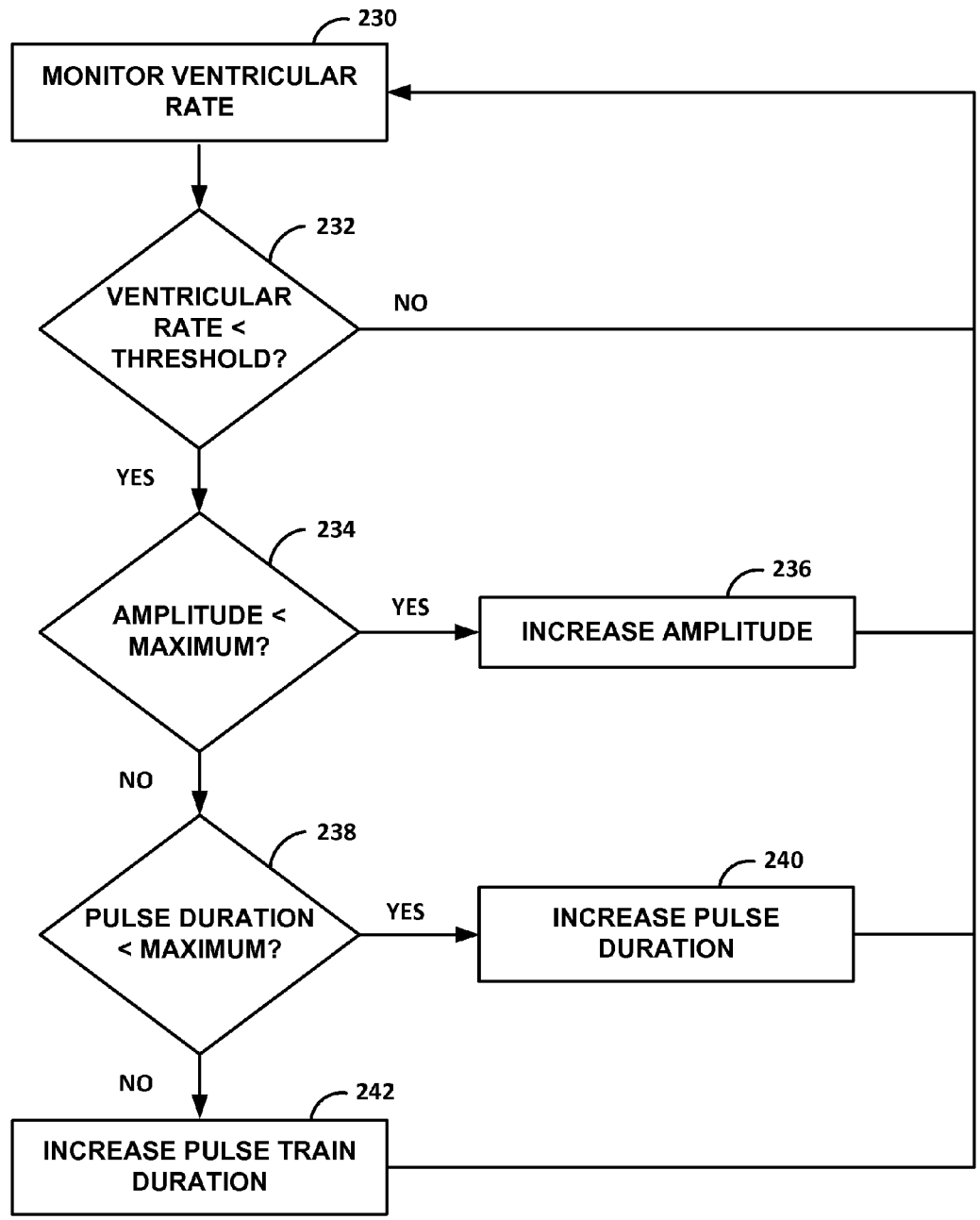
FIG. 8 is a flow diagram of an example method of closed-loop adjustment of vagal stimulation.

FIG. 8 is a flow diagram of an example method of closed-loop adjustment of AV nodal vagal stimulation. Processor 80 controls electrical sensing module 86 and/or sensor 87 to monitor one or more signals indicative of ventricular rate, e.g., via RV lead 18 and/or LV lead 20, and calculates a ventricular rate based on the sensed signals, e.g., based on indications of ventricular depolarizations received from electrical sensing module 86 (230). For example, processor 80 may calculate a mean ventricular rate over the first 30 seconds that signal generator 84 delivers AV nodal vagal stimulation.

Processor 80 determines whether the calculated ventricular rate is below a threshold (232). The threshold value may be based on a ventricular pacing rate, e.g., the rate at which RV 18 and LV 20 are paced if all of the ventricular contractions are paced. The comparison of the calculated ventricular rate to the threshold may indicate whether the AV nodal vagal stimulation delivered by signal generator 84 is satisfactory controlling the ventricular rate response. If the calculated ventricular rate is below the threshold, processor 80 may continue monitoring the ventricular rate (230).

If the calculated ventricular rate exceeds the threshold, processor 80 may adjust one or more stimulation parameters. For example, processor 80 may determine whether the stimulation amplitude is less than a maximum allowed stimulation amplitude (234). Memory 82 may store suitable ranges for one or more stimulation parameters, and processor 80 may determine whether a stimulation parameter is less than a maximum allowed value based on values stored within memory 82.

If the stimulation amplitude is less than the maximum allowed value, processor 80 may control signal generator 84 to increase the stimulation amplitude (236). For example, processor 80 may increase the stimulation amplitude by a specified amount or percentage. In some examples, the amount that processor 80 increments the stimulation amplitude is based on the calculated ventricular rate. After the stimulation amplitude is increased, processor 80 may monitor the ventricular rate to determine the impact of the new stimulation parameter values (230). For example, processor 80 may calculate a mean ventricular rate over the first 30 seconds that signal generator 84 delivers AV nodal vagal stimulation with the new set of stimulation parameter values.

If the target ventricular rate is not reached at the maximum stimulation amplitude, processor 80 may determine whether the pulse duration is less than a maximum allowed pulse duration (238). If the pulse duration is less than the maximum allowed value, e.g., 1.5 milliseconds, processor 80 may control signal generator 84 to increase the pulse duration (240). After the pulse duration is increased, processor 80 may monitor the ventricular rate to determine the impact of the new stimulation parameter values (230).

If target ventricular rate is not reached at the maximum amplitude and maximum pulse duration, processor 80 may control signal generator 84 to increase the pulse train duration (242). In some examples, processor 80 may increase the pulse train duration up to a maximum values, e.g., 400 milliseconds. If the target ventricular rate is not reached at the maximum pulse train duration, processor 80 may provide a continuous stream of pulses for a programmable duration of intervention rather than a burst pattern that includes a plurality of pulse trains.

FIG. 8 illustrates one example method of adjusting AV nodal vagal stimulation parameter values. In other examples, processor 80 may adjust other stimulation parameters, e.g., pulse duration, pulse train duration, pulse amplitude, pulse frequency, and pulse train frequency. Furthermore, processor 80 may adjust any parameters described herein in any suitable order. As another alternative, processor 80 may monitor the percentage of ventricular contractions that are paced and/or the percentage of ventricular depolarizations that are sensed, rather than the ventricular rate, to determine the extent to which the AV nodal vagal stimulation is controlling ventricular rate response, and whether adjustment of the AV nodal vagal stimulation parameter values is necessary.

During the interval between pulse trains, processor 80 may control electrical sensing module 86 and/or sensor 87 to monitor one or more signals indicative of atrial rhythm, e.g., via RA lead 22, to determine whether the atrial tachyarrhythmia persists. Processor 80 may control signal generator 84 to cease AV nodal vagal stimulation if the atrial arrhythmia has terminated.

To avoid prolonged and unnecessary AV nodal vagal stimulation and power source consumption, processor 80 may periodically control signal generator 84 to suspend AV nodal vagal stimulation to verify that the extent of ventricular pacing is insufficient and/or the ventricular rate exceeds the target ventricular rate without AV nodal vagal stimulation. As one example, processor 80 may control signal generator 84 to cease AV nodal vagal stimulation approximately every 15 minutes to monitor the percentage of ventricular contractions that are paced, the percentage of ventricular contractions that are sensed, and/or the ventricular rate without AV nodal vagal stimulation. Electrical sensing module 86, e.g., via RV lead 18 and/or LV lead 20, may monitor the percentage of ventricular contractions that are paced, the percentage of ventricular contractions that are sensed, and/or the ventricular rate without AV nodal vagal stimulation. Processor 80 may control signal generator 86 to reinitiate AV nodal vagal stimulation based on the percentage of ventricular contractions that are paced, the percentage of ventricular contractions that are sensed, and/or the ventricular rate.

In other examples, signal generator 82 may deliver AV nodal vagal stimulation at all times, regardless of whether an atrial arrhythmia is detected. This type of prolonged AV nodal vagal stimulation may be useful if a large and/or continuous modulation of autonomic tone is desirable. For example, prolonged AV nodal vagal stimulation may be used to increase parasympathetic tone, e.g., if electrical sensing module 86 and/or sensor 87 detects elevated sympathetic and/or decreased parasympathetic autonomic activity.

In some examples, signal generator 82 may deliver AV nodal or other forms of vagal stimulation during sinus rhythm, e.g., in addition or as an alternative to in response to a detected atrial tachyarrhythmia. The vagal tone augmentation provided by AV nodal vagal stimulation may improve long-term left ventricular reverse remodeling and decrease atrial and ventricular arrhythmic burden in heart failure patients. Vagal stimulation may also provide positive neuroendocrinal modulation.

As one example, processor 80 may control signal generator 82 to deliver vagal stimulation in the form of bursts of high frequency pulses using RA lead 22 during the effective atrial refractory period of heart 12. In such examples, the duration of each burst of pulses may be less than approximately 180 milliseconds. Each burst of pulses may be triggered based on an intrinsic atrial depolarization or a paced atrial event. These timing parameters may help ensure that each burst is contained to the effective atrial refractory period and does not induce an atrial arrhythmia.

In some examples, one device, e.g., IMD 16, may deliver vagal stimulation during a rapidly conducting atrial arrhythmia to decrease a ventricular rate response and deliver vagal stimulation during sinus rhythm to influence vagal modulation. In this manner, a single device may combine the neuro-endocrinal modulation effects due to vagal stimulation and CRT.

In some patients that do not experience rapidly conducing atrial arrhythmias, signal generator 82 may deliver vagal stimulation during the effective atrial refractory period of heart 12, e.g., during sinus rhythm and/or non-rapidly conducing atrial arrhythmias. Vagal stimulation may produce positive effects, e.g., left ventricular reverse remodeling and/or neuro-endorinal modulation. Therefore, IMD 16 may deliver vagal stimulation to heart failure patients receiving CRT and/or other heart failure patients regardless of whether the patients experience a rapidly conducting atrial arrhythmia.

IMD 16 may include various safety features to ensure that AV nodal vagal stimulation is only delivered when appropriate. For example, if, based on signals received from electrical sensing module 86 and/or sensor 87, processor 80 detects the onset of a ventricular arrhythmia during AV nodal vagal stimulation, processor 80 may disable AV nodal vagal stimulation, e.g., until reprogramming by a clinician via external programmer 24. As another example, if processor 80 detects an interval between a paced atrial event and an intrinsic ventricular depolarization less than a tachyarrhythmia threshold, e.g., approximately 80 milliseconds, processor 80 may disable AV nodal vagal stimulation.

IMD 16 may also prevent AV nodal vagal stimulation if processor 80 detects a possible lead dislodgement. As one example, if during automatic measurement, e.g., daily, of the atrial pacing threshold, electrical sensing module 86 and/or sensor 87 does not observe atrial capture at the highest voltage, processor 80 may disable AV nodal vagal stimulation, e.g., until reprogramming by a clinician via external programmer 24. As another example, if electrical sensing module 86 and/or sensor 87 detects an abrupt change in atrial impedance, processor 80 may disable AV nodal vagal stimulation, e.g., until reprogramming by a clinician via external programmer 24. As yet another example, processor 80 may prevent use of AV nodal stimulation during a specified time period following lead implantation, e.g., approximately one month, in case of acute lead dislodgement. For example, processor 80 may not permit AV nodal vagal stimulation or may require approval from a user, e.g., a clinician, via external programmer 24 prior to initiating AV nodal vagal stimulation. In other examples, external programmer 24 may load AV nodal vagal stimulation programming into memory 82 after acute lead dislodgement is no longer a concern.

Figure 9:
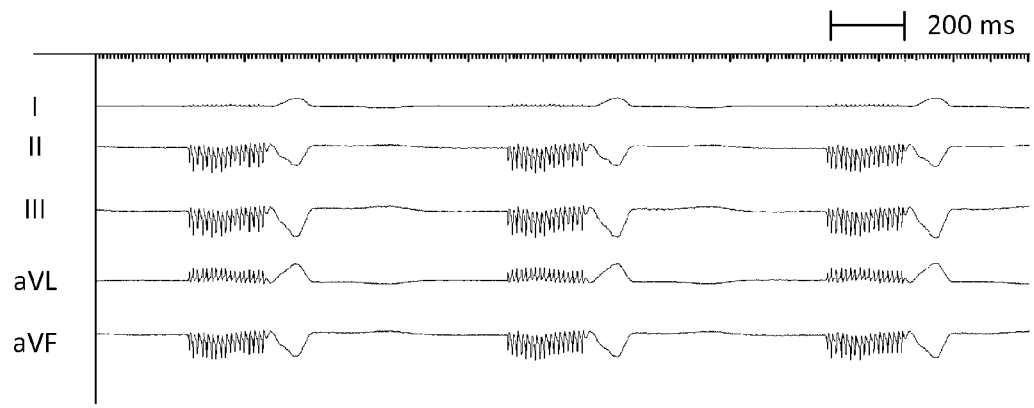
FIGS. 9-12 illustrate example electrocardiogram outputs obtained during AV nodal vagal stimulation.

FIGS. 9-12 illustrate example electrocardiogram outputs obtained during AV nodal vagal stimulation. The artifacts illustrated in FIGS. 9-12 correspond to the delivery of high frequency AV nodal vagal stimulation. In each of FIGS. 9-11, burst of high frequency vagal stimulation pulses were delivered during the effective atrial refractory period to decrease the AV node conduction, e.g., prolong the PR interval or cause AV block, without undesirable atrial arrhythmia induction. In FIG. 9, AV nodal vagal stimulation was delivered with trains of pulses, each pulse having an amplitude of 5 volts. The duration of each burst of pulses was less than the effective atrial refractory period, e.g., less than approximately 180 milliseconds. No effects on AV conduction resulted.

Figure 10:
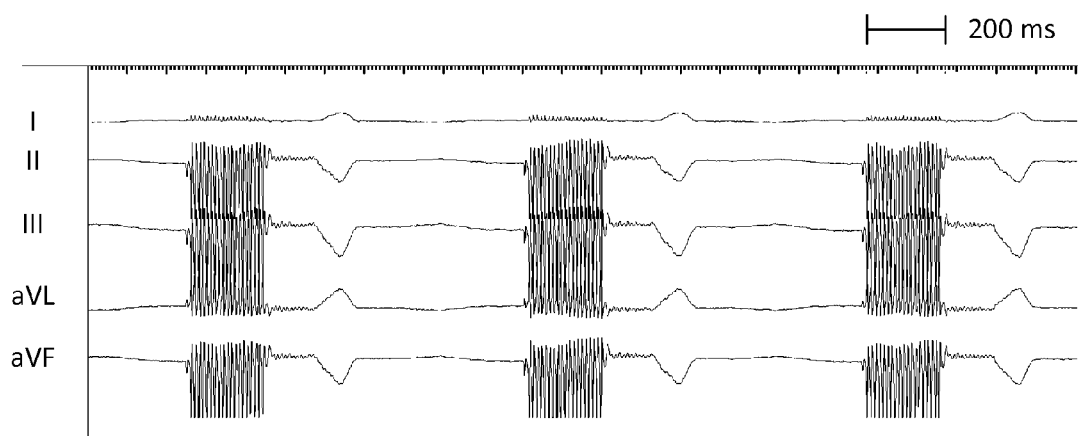
Figure 11:
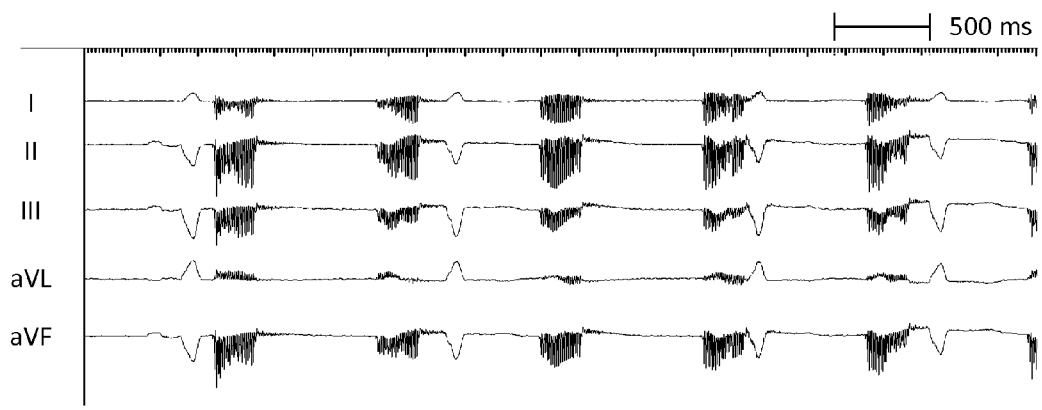

In FIG. 10, AV nodal vagal stimulation was delivered with trains of pulses, each pulse having an amplitude of 8 volts. An increase in the interval between the P-wave corresponding the atrial depolarization and the R-wave corresponding to ventricular depolarization resulted. In FIG. 11, AV nodal vagal stimulation was delivered with trains of pulses, each pulse having an amplitude of 9 volts. A 2:1 AV block resulted. In other examples, first degree, second degree, and third degree AV block may be achieved using AV nodal vagal stimulation.

Figure 12:
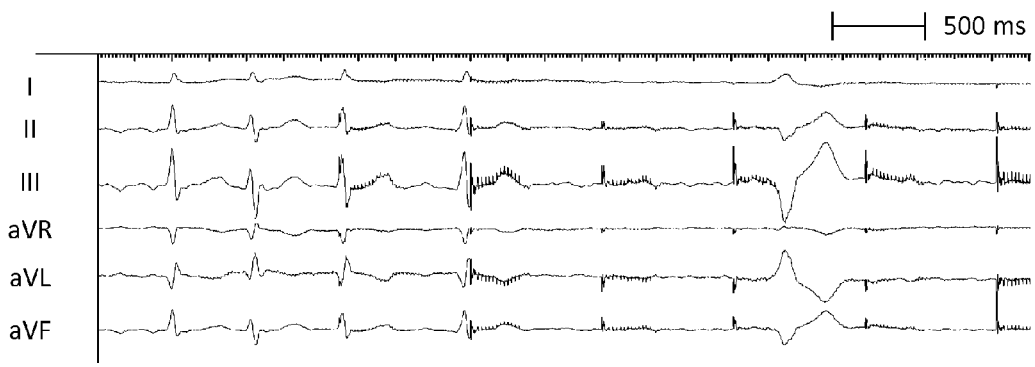

In FIG. 12, AV nodal vagal stimulation was delivered using trains of pulses during atrial fibrillation. The AV nodal vagal stimulation was successful in providing complete AV block during atrial fibrillation.

Various examples have been described. Some examples provide transcatheter control of the cardiac autonomic nervous system during atrial tachyarrhythmia to control ventricular rate response and facilitate CRT. The transcatheter control may comprise asynchronous (e.g., continuous or intermittent) and triggered selective vagal stimulation by stimulation of the AV nodal region through a single endocardial screw-in lead that provides atrial pacing/sensing as well as the AV nodal vagal stimulation. These and other examples are within the scope of the following claims.

The invention claimed is:

1. A method for modulating the autonomic nervous system of a patient via an implantable medical device, the method comprising:
   detecting, by the implantable medical device, an atrial depolarization via at least one electrode of a right atrial lead coupled to the implantable medical device, the at least one electrode of the right atrial lead implanted within a right atrium of a heart of the patient;
   determining, by the implantable medical device, that the heart is in sinus rhythm; and
   in response to detecting the atrial depolarization and determining that the heart is in sinus rhythm, delivering, by the implantable medical device and via the at least one electrode of the right atrial lead, vagal stimulation during an atrial refractory period subsequent to the detected atrial depolarization, wherein the vagal stimulation is configured to modulate the autonomic nervous system of the patient, and wherein the vagal stimulation is configured to at least one of increase ventricular reverse remodeling or decrease arrhythmic burden of the patient.

2. The method of claim 1,
   wherein the implantable medical device is coupled to at least one ventricular lead, the ventricular lead comprising at least one electrode located within a ventricle of the heart, and
   wherein determining that the heart is sinus rhythm comprises:
      detecting, by the implantable medical device, a plurality of ventricular depolarizations via the electrode of the ventricular lead; and
      determining that the heart is in sinus rhythm based on the ventricular depolarizations.

3. The method of claim 1,
   wherein the implantable medical device is coupled to at least one ventricular lead, the ventricular lead comprising at least one electrode located within a ventricle of the heart,
   the method further comprising delivering, by the implantable medical device, cardiac resynchronization therapy via the at least one electrode of the at least one ventricular lead.

4. The method of claim 3,
   wherein the implantable medical device is coupled to at least two ventricular leads, each of the ventricular leads comprising a respective electrode within a respective ventricle of the heart,
   the method further comprising delivering, by the implantable medical device, cardiac resynchronization therapy via the electrodes of the at least two ventricular leads.

5. The method of claim 1,
   further comprising determining, by the implantable medical device, that the heart is in a non-rapidly conducting atrial arrhythmia,
   wherein delivering vagal stimulation comprises delivering vagal stimulation in response to the determination.

6. The method of claim 1, wherein the vagal stimulation is configured to at least one of modulate autonomic tone of the patient, provide positive neuro-endocrinal modulation, or increase parasympathetic activity.

7. The method of claim 1,
   wherein detecting an atrial depolarization comprises detecting a plurality of consecutive atrial depolarizations via the at least one electrode of the right atrial lead, and
   wherein delivering vagal stimulation comprises chronically delivering bursts of vagal stimulation in response to each of the detected atrial depolarizations, each of the bursts delivered during a respective atrial refractory period subsequent to the respective atrial depolarization.

8. The method of claim 1,
   wherein detecting an atrial depolarization comprises detecting a plurality of consecutive atrial depolarizations via the at least one electrode of the right atrial lead,
   the method further comprising detecting, by the implantable medical device, at least one of elevated sympathetic autonomic activity or decreased parasympathetic autonomic activity, and
   wherein delivering vagal stimulation comprises delivering, in response to the detection, bursts of vagal stimulation in response to each of the detected atrial depolarizations, each of the bursts delivered during a respective atrial refractory period subsequent to the respective atrial depolarization.

9. The method of claim 1, wherein delivering vagal stimulation comprises delivering a plurality of pulse trains, each of the pulse trains comprising a plurality of pulses.

10. The method of claim 9, wherein delivering a plurality of pulse trains comprises delivering pulse trains at a pulse train frequency within a range from approximately 40 pulse trains per minute to approximately 140 pulse trains per minute, a pulse train duration within a range from less than approximately 180 milliseconds to approximately 400 milliseconds, and a pulse duration within a range from approximately 0.2 milliseconds to 1.5 milliseconds.

11. The method of claim 10, wherein delivering a plurality of pulse trains comprises delivering pulse trains at a pulse duration of approximately 0.2 milliseconds, a pulse train duration of approximately 250 milliseconds, a pulse amplitude of approximately 4 volts, a pulse frequency of approximately 50 Hertz, and a pulse train frequency of approximately 80 pulse trains per minute.

12. The method of claim 10, wherein delivering a plurality of pulse trains comprises delivering pulse trains at a pulse train duration of less than approximately 180 milliseconds.

13. The method of claim 1, wherein delivering vagal stimulation comprises delivering atrioventricular nodal vagal stimulation.

14. The method of claim 13, wherein delivering atrioventricular nodal vagal stimulation comprises delivering stimulation to an AV nodal vagal fat pad of the patient.

15. The method of claim 1, further comprising delivering, by the implantable medical device, pacing pulses to the right atrium via the electrode.

16. The method of claim 1, wherein the electrode is located posteriorly to a coronary sinus ostium of the heart and along a septum that separates the right atrium and a left atrium of the heart.

17. The method of claim 16, wherein the electrode comprises a helix tip electrode configured to fixate the electrode posteriorly to the coronary sinus ostium of the heart and along the septum that separates the right atrium and a left atrium of the heart.

18. The method of claim 1, further comprising:
detecting, by the implantable medical device, a ventricular rate subsequent to delivering the vagal stimulation; and
modifying, by the implantable medical device, a stimulation parameter of the vagal stimulation if the ventricular rate is above a threshold.

19. The method of claim 1, further comprising:
detecting, by the implantable medical device, at least one PR interval subsequent to delivering the vagal stimulation; and
modifying, by the implantable medical device, the stimulation parameter of the vagal stimulation if the PR interval is below a threshold.

20. The method of claim 1, wherein the vagal stimulation is configured to increase ventricular reverse remodeling.

21. The method of claim 1, wherein the vagal stimulation is configured to decrease arrhythmic burden of the patient.

22. A system for modulating the autonomic nervous system of a patient, the system comprising:
a right atrial lead comprising at least one electrode configured for implantation within a right atrium of a heart of the patient; and
an implantable medical device coupled to the right atrial lead, the implantable medical device configured to:
detect an atrial depolarization via at least one electrode of a right atrial lead coupled to the implantable medical device, the at least one electrode of the right atrial lead implanted within a right atrium of a heart of the patient;
determine that the heart is in sinus rhythm;
in response to the detected atrial depolarization and the determination that the heart is in sinus rhythm, deliver via the at least one electrode of the right atrial lead, vagal stimulation during an atrial refractory period subsequent to the detected atrial depolarization, wherein the vagal stimulation is configured to modulate the autonomic nervous system of the patient, and wherein the vagal stimulation is configured to at least one of increase ventricular reverse remodeling or decrease arrhythmic burden of the patient.

23. The system of claim 22, wherein the implantable medical device is configured to determine that the heart is in non-rapidly conducting atrial arrhythmia, and deliver vagal stimulation in response to the determination.

24. The system of claim 22, wherein the vagal stimulation is configured to at least one of modulate autonomic tone of the patient, provide positive neuro-endocrinal modulation, or increase parasympathetic activity.

25. The system of claim 22, wherein the implantable medical device is configured to detect a plurality of consecutive atrial depolarizations via the at least one electrode of the right atrial lead, and chronically deliver bursts of vagal stimulation in response to each of the detected atrial depolarizations, each of the bursts delivered during a respective atrial refractory period subsequent to the respective atrial depolarization.

26. The system of claim 22, wherein the vagal stimulation comprises atrioventricular nodal vagal stimulation.

27. The system of claim 26, wherein the electrode is configured to deliver stimulation to an AV nodal vagal fat pad of the patient.

28. The system of claim 22, wherein the electrode is configured for location posteriorly to a coronary sinus ostium of the heart and along a septum that separates the right atrium and a left atrium of the heart.

29. The system of claim 28, wherein the electrode comprises a helix tip electrode configured to fixate the electrode posteriorly to the coronary sinus ostium of the heart and along the septum that separates the right atrium and a left atrium of the heart.

30. A system for modulating the autonomic nervous system of a patient, the system comprising:
means for detecting an atrial depolarization via at least one electrode implanted within a right atrium of a heart of the patient;
means for determining that the heart is in sinus rhythm;
means for, in response to the detected atrial depolarization and the determination that the heart is in sinus rhythm, delivering, via the at least one electrode, vagal stimulation during an atrial refractory period subsequent to the detected atrial depolarization, wherein the vagal stimulation is configured to modulate the autonomic nervous system of the patient, and wherein the vagal stimulation is configured to at least one of increase ventricular reverse remodeling or decrease arrhythmic burden of the patient.

* * * * *

UNITED STATES PATENT AND TRADEMARK OFFICE
CERTIFICATE OF CORRECTION

PATENT NO. : 8,731,663 B2
APPLICATION NO. : 13/749438
DATED : May 20, 2014
INVENTOR(S) : Stefano Bianchi et al.

It is certified that error appears in the above-identified patent and that said Letters Patent is hereby corrected as shown below:

In the Claims

Col. 17, line 61, delete "determining that the heart is sinus rhythm" and insert in place thereof
-- determining that the heart is in sinus rhythm --.

Signed and Sealed this
Twenty-first Day of April, 2015

Michelle K. Lee
*Director of the United States Patent and Trademark Office*